US012605346B2

(12) United States Patent
Itoh et al.

(10) Patent No.: US 12,605,346 B2
(45) Date of Patent: Apr. 21, 2026

(54) COMPOSITION CONTAINING CURCUMIN COMPOUND, AND METHOD FOR PRODUCING SAME

(71) Applicant: THERABIOPHARMA INC., Kawasaki (JP)

(72) Inventors: Masashi Itoh, Kawasaki (JP); Satoshi Nishimura, Kawasaki (JP); Tatsuya Ogawa, Kawasaki (JP); Tadashi Hashimoto, Kawasaki (JP)

(73) Assignee: THERABIOPHARMA INC., Kawasaki (JP)

( * ) Notice: Subject to any disclaimer, the term of this patent is extended or adjusted under 35 U.S.C. 154(b) by 857 days.

(21) Appl. No.: 17/759,610

(22) PCT Filed: Jan. 25, 2021

(86) PCT No.: PCT/JP2021/002393

§ 371 (c)(1),
(2) Date: Jul. 27, 2022

(87) PCT Pub. No.: WO2021/153485

PCT Pub. Date: Aug. 5, 2021

(65) Prior Publication Data

US 2023/0084246 A1 Mar. 16, 2023

(30) Foreign Application Priority Data

Jan. 27, 2020 (JP) ................................ 2020-010544

(51) Int. Cl.
*A61K 31/121* (2006.01)
*A61K 9/14* (2006.01)
*A61K 9/16* (2006.01)

(52) U.S. Cl.
CPC .......... *A61K 31/121* (2013.01); *A61K 9/1652* (2013.01); *A61K 9/14* (2013.01)

(58) Field of Classification Search
None
See application file for complete search history.

(56) References Cited

U.S. PATENT DOCUMENTS

2010/0249063 A1* 9/2010 Sugama .................. A61P 19/02 544/80
2011/0274809 A1 11/2011 Miuchi et al.
(Continued)

FOREIGN PATENT DOCUMENTS

CN 102843919 A 12/2012
CN 109562118 A 4/2019
(Continued)

OTHER PUBLICATIONS

Athira et al. "Water Soluble Octenyl Succinylated Cassava Starch-Curcumin Nanoformulation With Enhanced Bioavailability and Anticancer Potential", Starch—Stärke, 2018, 70: 1700178, pp. 1-9. (Year: 2018).*
(Continued)

*Primary Examiner* — Carlos A Azpuru
*Assistant Examiner* — Casey S Hagopian
(74) *Attorney, Agent, or Firm* — Oblon, McClelland, Maier & Neustadt, L.L.P.

(57) ABSTRACT

Provided are a novel amorphous curcumin compound powdery composition that is inexpensive, is improved in bioabsorbability and bioavailability of curcumin, and has long-term stability, and a method for producing the powdery composition. The present invention relates to a powdery composition containing an amorphous curcumin compound and a hydrophilic modified starch and having a Raman spectrum including one or more peaks at wavenumbers of 1630, 1599, 1428, and 1243 (expressed in ±2 $cm^{-1}$) and a method for producing the powdery composition.

7 Claims, 2 Drawing Sheets

(56) References Cited

U.S. PATENT DOCUMENTS

| | | | |
|---|---|---|---|
| 2017/0239194 | A1 | 8/2017 | Takeuchi et al. |
| 2018/0289635 | A1 | 10/2018 | Nakao et al. |
| 2019/0200660 | A1 | 7/2019 | Miyamoto et al. |
| 2019/0224325 | A1 | 7/2019 | Kakeya et al. |
| 2019/0350233 | A1 | 11/2019 | Frecker et al. |
| 2019/0351401 | A1 | 11/2019 | Takahata et al. |
| 2019/0380976 | A1 | 12/2019 | Nagano et al. |
| 2020/0009211 | A1 | 1/2020 | Nagano et al. |
| 2020/0254105 | A1 | 8/2020 | Kakeya et al. |
| 2021/0008007 | A1 | 1/2021 | Makino et al. |
| 2021/0213094 | A1 | 7/2021 | Jacob et al. |

FOREIGN PATENT DOCUMENTS

| | | | | |
|---|---|---|---|---|
| CN | 110381932 A | 10/2019 | | |
| JP | WO 2016/010093 A1 | 1/2016 | | |
| JP | WO 2017/061627 A1 | 4/2017 | | |
| JP | WO 2018/056444 A1 | 3/2018 | | |
| JP | WO 2018/159852 A1 | 9/2018 | | |
| JP | WO 2019/160146 A1 | 8/2019 | | |
| WO | WO-2011129284 A1 * | 10/2011 | .......... | A23L 29/212 |
| WO | WO 2015/174475 A1 | 11/2015 | | |
| WO | WO 2018/003587 A1 | 1/2018 | | |
| WO | WO 2018/159853 A1 | 9/2018 | | |
| WO | WO 2019/202547 A1 | 10/2019 | | |

OTHER PUBLICATIONS

Machine translation of WO 2011/129284 A1, Oct. 20, 2011. (Year: 2011).*

Combined Chinese Office Action and Search Report issued Jun. 1, 2023 in Chinese Application 202180011742.2, (with unedited computer-generated English translation), 21 pages.

Extended European Search Report issued Jul. 10, 2023 in European Application No. 21748215.7, 8 pages.

Sanphui, P. et al., "Curcumin—a biological wonder molecule: A crystal engineering point of review", Cryst. Growth Des., DOI: 10.1021/acs.cgd.8b00646, Jul. 25, 2018, total 59 pages.

Pawar Y et al. "Phase behavior and oral bioavailability of amorphous curcumin", European Journal of Pharmaceutical Sciences, vol. 47, 2012, pp. 56-64.

Athira G et al. "Water Soluble Octenyl Succinylated Cassava Starch-Curcumin Nanoformulation With Enhanced Bioavailability and Anticancer Potential", Starch, 2018, pp. 1-9.

Liu, D., "Engineering nano-curcumin with enhanced solubility and in-vitro anti-cancer bioactivity", 2013, pp. 1-53.

Araki et al. "Application of a Microreactor to Pharmaceutical Manufacturing; Preparation of Amorphous Curcumin Nanoparticles and Controlling the Crystallinity of Curcumin Nanoparticles by Ultrasonic Treatment", AAPS PharmSciTech, vol. 21. No. 17, 2020.

Rahma et al. "Intermolecular Interactions and the Release Pattern of Electrospun Curcumin-Polyvinyl (pyrrolidone) Fiber", Biol. Pharm. Bull., vol. 39. No. 2, 2016, pp. 163-173.

Sanphui et al. "New polymorphs of curcumin" Chem. Commun., vol. 47, 2011, pp. 5013-5015.

He et al. "Molecular Interactions for the curcumin-polymer complex, with Enhanced Anti-Inflammatory Effects", Pharmaceutics, vol. 11. No. 442, 2019, pp. 1-21.

International Search Report issued on Mar. 30, 2021, in PCT/JP2021/002393 filed on Jan. 25, 2021.

International Preliminary Report on Patentability issued on Feb. 1, 2022 in PCT/JP2021/002393 filed on Jan. 25, 2021 (with English translation), 10 pages.

* cited by examiner

COMPOSITION CONTAINING CURCUMIN COMPOUND, AND METHOD FOR PRODUCING SAME

This application is a national stage application of PCT/JP2021/002393, filed Jan. 25, 2021, which claims benefit of Japanese application 2020-010544, filed Jan. 27, 2020. The entire contents of both applications are incorporated by reference and priority is claimed to both applications.

FIELD OF THE INVENTION

The present invention relates to an amorphous curcumin compound-containing powdery composition, and a method for producing the powdery composition.

BACKGROUND OF THE INVENTION

Curcumin recently has been shown to have pharmacological effects, such as a tumor formation inhibition effect, an antioxidant effect, an anti-inflammatory effect, a hypocholesterolemic effect, an anti-allergic effect, a brain disease preventive effect, and a cardiac disease preventive and therapeutic effect, and has been studied to find its application in foods (e.g., functional foods), medicines, and cosmetics.

One of methods for improving the absorbability of curcumin includes forming a complex of curcumin containing amorphous curcumin and/or its analog and hydroxypropyl methylcellulose and/or hydroxypropyl cellulose in order to improve the absorbability into the body through oral intake (Patent Literature 1).

Sanphui, P et al. has reported production methods, chemical and steric structures, NMR, PXRD, and SEM images, solubility, and the situation of in-vivo clinical research of, for example, curcumin Forms 1 to 3 and amorphous curcumin, regarding crystalline polymorphism of curcumin from the perspective of crystal engineering. This report describes that amorphous curcumin is obtained by melting curcumin, followed by cooling at room temperature or freeze cooling, and a sample stored in a container is generally stable under normal conditions (temperature 20° C. to 35° C., humidity 40% to 70%) till 6 months (Non Patent Literature 1).

Pawar, Y. B. et al. has specified the thermodynamic and kinetic parameters of amorphous curcumin and reported the Cmax and AUC of amorphous curcumin. It also has been reported that the theoretically predicted aqueous solubility advantage and oral bioavailability advantage from amorphous curcumin are not achieved due to water-induced devitrification of glassy amorphous curcumin (Non Patent Literature 2).

CITATION LIST

Patent Literature

Patent Literature 1: WO 2015/174475 A

Non Patent Literature

Non Patent Literature 1: Sanphui, P et al. Curcumin-a biological wonder molecule: A crystal engineering point of review, Cryst. Growth Des, Publication Date(Web): 25 Jul. 2018

Non Patent Literature 2: Pawar, Y. B. et al., Phase behavior and oral bioavailability of amorphous Curcumin, Euro. J. of Pharmaceutical Sciences, 47 (2012) 56-64)

SUMMARY OF THE INVENTION

Technical Problem

As described above, various approaches have been explored to improve the stability and absorbability of curcumin compounds useful in foods and drug.

However, there is still a need to provide curcumin compounds that are produced industrially efficiently, have good storage stability and other properties, and have high absorbability and immediate effect.

Specifically, the present invention is directed to a novel amorphous curcumin compound-containing powdery composition that is inexpensive, is improved in bioabsorbability and bioavailability of the curcumin compound, and has long-term stability; and a method for producing the powdery composition.

Solution to Problem

The inventors of the present invention intensively studied a novel amorphous curcumin compound powdery composition and a method for producing the powdery composition and found that a powdery composition containing an amorphous curcumin compound and a hydrophilic modified starch and exhibiting high efficiency, stability, and absorbability is produced by subjecting an amorphous curcumin compound obtained by heat-melting a curcumin compound to wet grinding together with hydrophilic modified starch, and then powdering the wet-ground amorphous curcumin, completing the present invention.

Specifically, the present invention provides the following [1] to [12].

[1] A powdery composition containing an amorphous curcumin compound and a hydrophilic modified starch and having a Raman spectrum including one or more peaks at wavenumbers of 1630, 1599, 1428, and 1243 (expressed in $\pm 2\ cm^{-1}$).

[2] The powdery composition according to [1] having a Raman spectrum including peaks at wavenumbers of 1630, 1599, 1428, and 1243 (expressed in $\pm 2\ cm^{-1}$).

[3] The powdery composition according to [1] or [2] having a Raman spectrum substantially in accordance with FIG. 1.

[4] The powdery composition according to any one of [1] to [3] having an X-ray powder diffraction (XRPD) pattern substantially in accordance with FIG. 2.

[5] The powdery composition according to any one of [1] to [4], wherein the curcumin compound is at least one selected from curcumin, bisdemethoxycurcumin, demethoxycurcumin, and tetrahydrocurcumin.

[6] The powdery composition according to any one of [1] to [5], wherein a weight ratio of the amorphous curcumin compound to the hydrophilic modified starch is 1:2 to 2:1.

[7] The powdery composition according to any one of [1] to [6], wherein a weight ratio of the amorphous curcumin compound to the hydrophilic modified starch is 1:1.8 to 1.8:1.

[8] A method for producing the powdery composition according to any one of [1] to [7], the method including wet-grinding a mixture of an amorphous curcumin compound and a hydrophilic modified starch, and then forming a fine powder from the wet-ground mixture.

[9] The production method according to [8], wherein the amorphous curcumin compound is obtained by heat-melting a curcumin compound and then roughly grinding the curcumin compound.

[10] The production method according to [8] or [9], wherein a process for forming the fine powder involves freeze drying.

[11] The production method according to any one of [8] to [10], wherein a mixing weight ratio of the amorphous curcumin compound to the hydrophilic modified starch is 1:2 to 2:1.

[12] The production method according to any one of [8] to [11], wherein a mixing weight ratio of the amorphous curcumin compound to the hydrophilic modified starch is 1:1.8 to 1.8:1.

Advantageous Effects of the Invention

The present invention can provide an amorphous curcumin compound-containing powdery composition that is simple and inexpensive and has improved stability and absorbability, and a method for producing the powdery composition.

DETAILED DESCRIPTION OF THE EMBODIMENTS

Figure 1:
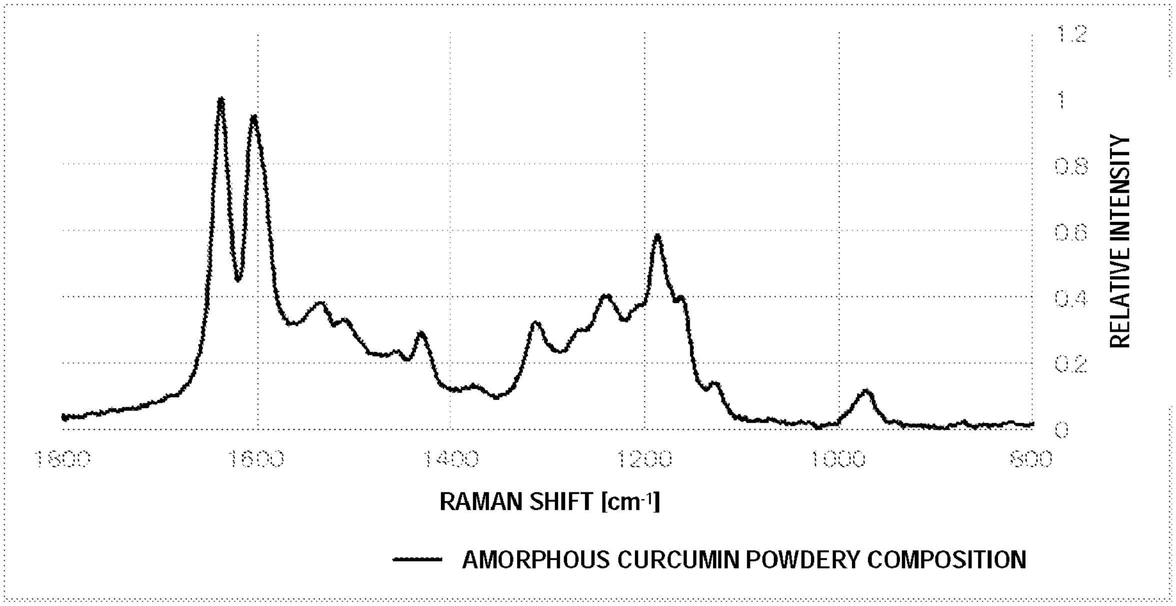
FIG. 1 is a Raman spectrum of an amorphous curcumin compound-containing powdery composition of the present invention.

Examples of the curcumin compound in the present invention include curcumin and curcumin analogs, such as bisdemethoxycurcumin, demethoxycurcumin, and tetrahydrocurcumin. The curcumin compound in the present invention is preferably curcumin among these curcumin compounds.

Curcumin is a main component of curcuminoids (curcumin, demethoxycurcumin, bisdemethoxycurcumin, and tetrahydrocurcumin) contained in a turmeric pigment and is a compound represented by the following structural formula.

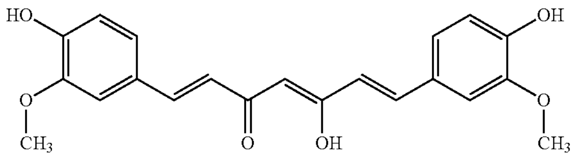 [SMILES: COc1cc(/C=C/C(=O)/C=C(O)/C=C/c2ccc(O)c(OC)c2)ccc1O]

Curcumin in the present invention may be chemically synthesized curcumin or may be curcumin distributed as a turmeric pigment. Examples of turmeric pigments include a turmeric powder made from dried rhizomes of plants belonging to the genus Curcuma of the family Zingiberaceae (e.g., Curcuma longa LINNE), crude curcumin or oleoresin (turmeric oleoresin) obtained by extracting the turmeric powder with an appropriate solvent (e.g., ethanol, oils and fats, propylene glycol, hexane, acetone), and purified curcumin.

Curcumin includes two tautomeric forms, keto and enol.

[Hydrophilic Modified Starch]

The hydrophilic modified starch used in the present invention is at least one selected from the group consisting of acetylated distarch adipate, acetylated distarch phosphate, acetylated oxidized starch, starch sodium octenyl succinate, starch acetate, oxidized starch, hydroxypropyl starch, hydroxypropyl distarch phosphate, phosphated distarch phosphate, monostarch phosphate, distarch phosphate, sodium starch glycolate.

The hydrophilic modified starch in the present invention is more preferably starch sodium octenyl succinate among these hydrophilic modified starches in order to provide high absorbability and storage stability and stabilize amorphous curcumin with a small amount.

With regard to the ratio of the amorphous curcumin compound to the hydrophilic modified starch, specifically, the mass ratio of amorphous curcumin compound: hydrophilic modified starch is preferably from 1:100 to 100:1, and more preferably from 1:10 to 10:1, further more preferably from 1:2 to 2:1, even more preferably from 1:1.8 to 1.8:1 in terms of, for example, costs, bioabsorbability, storage stability, low dose, and administration to human.

[Powdery Composition of Present Invention]

In the powdery composition of the present invention, the curcumin compound is stably present as an amorphous curcumin compound. Amorphous curcumin compounds known in the related art are crystallized during long-term storage, but the curcumin compound in the composition of the present invention is maintained in an amorphous state even after long-term storage.

The powdery composition of the present invention has a Raman spectrum including one or more peaks at wavenumbers of 1630, 1599, 1428, and 1243 (expressed in ±2 $cm^{-1}$).

The Raman spectrum is preferably a Raman spectrum including peaks at wavenumbers of 1630, 1599, 1428, and 1243 (expressed in ±2 $cm^{-1}$). Furthermore, the Raman spectrum is preferably a Raman spectrum substantially in accordance with FIG. 1.

Figure 2:
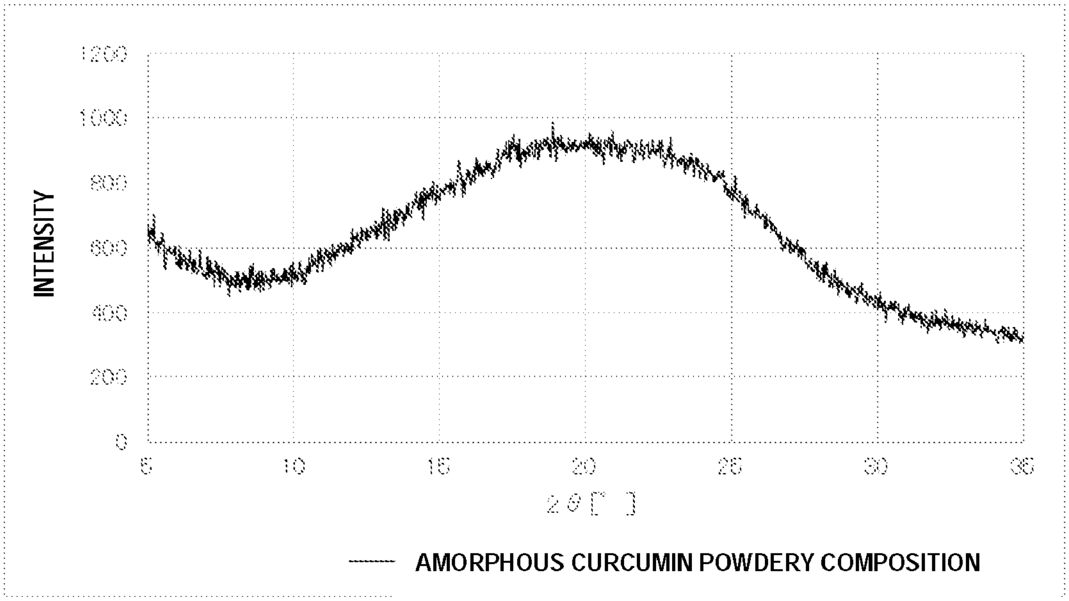
FIG. 2 is an X-ray diffraction pattern of the amorphous curcumin compound-containing powdery composition of the present invention recorded in the reflection/transmission mode.

The curcumin compound in the powdery composition of the present invention is amorphous and specifically has an X-ray powder diffraction (XRPD) pattern substantially in accordance with FIG. 2.

The average particle size of the powdery composition of the present invention is preferably from 0.1 to 500 μm, more preferably from 1 to 100 μm, further more preferably from 1 to 10 μm. The average particle size is measured by the laser diffraction scattering method.

[Method for Producing Powdery Composition of Present Invention]

The powdery composition of the present invention can be produced by wet-grinding a mixture of an amorphous curcumin compound and a hydrophilic polymer, and then forming a fine powder from the wet-ground mixture.

With regard to materials of the "curcumin compound", the curcumin compound may be a chemically synthesized curcumin compound or a curcumin compound derived from a turmeric pigment, as described above.

The amorphous curcumin compound can be obtained by heat-melting a curcumin lar, melting is preferably performed at from 180° C. to 250° C. for from 1 minute to 20 minutes, more preferably performed at from 180° C. to 230° C. for from 1 minute to 10 minutes. Heat-melting is usually followed by cooling to produce an amorphous curcumin compound. Specific examples of cooling include cooling by standing at room temperature or using, for example, air-cooling or liquid nitrogen. Of these, air-cooling is preferred in terms of costs. Air-cooling may be natural air cooling or forced air cooling, but preferably natural air cooling or forced air cooling with air at from 5° C. to 35° C.

Examples of the hydrophilic modified starch used include those described above. The mixing ratio of the amorphous curcumin compound to the hydrophilic modified starch is the same as described above.

The production method of the present invention includes wet-grinding a mixture of the amorphous curcumin compound prepared as described above and the hydrophilic modified starch.

Preferably, the amorphous curcumin compound is roughly ground in advance before wet grinding to improve the efficiency of the production method and the stability of the amorphous curcumin compound. Rough grinding is performed to the extent that the amorphous curcumin compound can be used in a wet-grinding machine. Examples of rough grinding means include grinders, such as blenders, ball mills, disc mills, pin mills, hammer mills, jet mills, atomizers, and masscolloiders.

Specifically, wet grinding in the present invention can be performed by using a grinder, such as a ball mill, a bead mill, a disc mill, a high-pressure homogenizer, a starburst, an in-line homogenizer, or a microfluidizer; and/or a friction grinder, such as a masscolloider. Of these machines, a bead mill or a ball mill is preferred, and a bead mill is more preferred because it is easy to produce a uniform powder.

Specific examples of aqueous media in wet grinding include methanol, hexane, ethanol, acetone, and water. Of these aqueous media, water is preferred.

Examples of fine powder-forming means following wet grinding include drying, such as evaporation drying, vacuum drying, spray drying, freeze drying, hot air drying, cool air drying, and air drying. Vacuum drying, spray drying, freeze drying, and air drying are preferred, and freeze drying is more preferred to improve absorbability and stability and shorten the time to the maximum blood concentration.

The powdery composition of the present invention can be used in the form of food. In this case, the powdery composition may further contain additives, such as polysaccharide thickeners, flavors, pigments, antioxidants, shelf-life improvers, preservatives [e.g., sodium benzoate], and sugars, unless the advantageous effects of the present invention are impaired.

The use of these additives can change various properties, including sensory properties, such as taste, flavor, and/or texture, and storage stability, and ease in handling, of the powdery composition of the present invention or a target to which these additives are added.

The powdery composition of the present invention when used in the form of therapeutic agent (medicine) may have any dosage form. For example, the powdery composition of the present invention can also be used as a liquid formulation or as a formulation prepared from a freeze-dried preparation just before use. The powdery composition of the present invention may be in a delayed release dosage form or an extended release dosage form. The powdery composition of the present invention can also be prepared by using additives, such as carriers and excipients commonly used for pharmaceutical formulations.

The administration route of the therapeutic agent of the present invention can be freely selected from systemic administration, local administration, oral administration, and parenteral administration depending on the disease, symptom, or other factors. Oral administration in a suitable dosage form, such as tablet, pill, capsule, granule, powder, or liquid, or parenteral administration in the form of injection (e.g., intravenous injection, intramuscular injection), suppository, transdermal agent, nasal agent, inhalation, or other forms can be selected depending on the administration method and route.

The therapeutic agent for oral administration according to the present invention may be a solid formulation, such as tablet, capsule, powder, or granule. These formulations are produced in accordance with a common method by mixing one or more active substances with an inert excipient, a lubricant, a disintegrant, a solubilizing agent, or other substances. The excipient may be, for example, lactose, cellulose, mannitol, or glucose. The lubricant may be, for example, magnesium stearate. The disintegrant may be, for example, sodium carboxymethyl starch. The tablet or pill may be coated with a sugar coating or a gastric or enteric coating as desired.

The therapeutic agent for oral administration may be a liquid formulation, such as a pharmacologically acceptable extract, emulsion, liquid, suspension, syrup, alcohol, or elixir. These formulations contain a common inert solvent (e.g., purified water or ethanol) and may further contain a solubilizer, a wetting agent, a suspending agent, a sweetener, a flavoring agent, a fragrance, a buffer (e.g., sodium citrate), a stabilizer, or a preservative.

The therapeutic agent for parenteral administration may be an injection, such as a sterile aqueous or non-aqueous liquid, a suspension, or an emulsion; an ointment or a lotion; a sublingual agent or oral patch for oral administration; or an aerosol for nasal administration, or a suppository.

The therapeutic agent in the form of injection can be administered by common intravenous injection, intraarterial injection, as well as intraarticular injection, subcutaneous injection, intradermal injection, intramuscular injection, or other injection. An aqueous solvent for the injection may be, for example, distilled water or saline. A non-aqueous solvent for the injection may be, for example, propylene glycol, polyethylene glycol, vegetable oils such as olive oil, alcohols such as ethanol, or Polysorbate 80 (name in Japanese Pharmacopoeia). These formulations may further contain an isotonic agent (e.g., sodium chloride, glucose), a preservative, a wetting agent, an emulsifier, a dispersant, a stabilizer, a pH adjuster (e.g., sodium citrate, sodium acetate, sodium phosphate), a buffer, a local anesthetic (e.g., procaine hydrochloride, lidocaine hydrochloride), or a solubilizing agent.

These formulations may be sterilized by, for example, filtration through a bacterial retention filter, addition of an antibacterial agent, or exposure to radiation. A composition prepared by dissolving or suspending a sterile solid composition in sterile water or a solvent for injection before use can also be used as these formulations. These formulations can be produced by a known method commonly used in the formulation process.

In the powdery composition of the present invention, the curcumin compound is in an amorphous state and has high long-term storage stability and high absorbability due to wet grinding unlike amorphous curcumin compounds known in the related art. In the powdery composition of the present invention, the curcumin compound is present in an amorphous state even after long-term storage. With regard to absorbability, not only the Cmax is high, but also the blood concentration reaches high levels in a short time so that the powdery composition of the present invention is quickly transferred to the target tissues. The powdery composition of the present invention also has the following properties: the mixing ratio of the hydrophilic modified starch to the amorphous curcumin is small, and the dose is thus small so that the blood concentration reaches high levels quickly.

The production method of the present invention can produce an intended amorphous curcumin compound-containing powdery composition at low costs because the process is simple. In addition, the powdery composition can have a high amorphous curcumin compound content.

Accordingly, the amorphous curcumin compound-containing powdery composition of the present invention is useful as pharmaceuticals, cosmetics, dietary supplements, functional foods, and foods for specified health use for introducing the bioactivity of curcumin compounds through oral administration.

EXAMPLES

The present invention will be described below in more detail by way of Examples; however, the present invention is not limited by these Examples.

[Example 1] Method for Producing Amorphous Curcumin Compound-Containing Powdery Composition of Present Invention

[Heat-Melting of Curcumin Compound and Other Process]

Natural curcumin (5 g) was flatly put in an aluminum dish, and the aluminum dish was placed on an electric griddle set at 220° C. to melt natural curcumin. After cooling at room temperature, the amorphous curcumin was subjected to dry grinding with an impact grinder to give a sample.

[Wet Grinding of Amorphous Curcumin Compound and Other Process]

The sample was mixed in accordance with the following formulation and then ground in a continuous horizontal-type ready mill RMH-03 (available from AIMEX Co., Ltd.), and the ground sample was freeze-dried for about 24 hours. The modified starch in Table 1 is starch sodium octenyl succinate.

TABLE 1

| | g |
|---|---|
| Sample (heat-melted product) | 12.0 |
| Modified starch | 9.6 |
| Water | 278.4 |
| Total | 300 |

[Test Example 1] Physical Measurement of Powdery Composition of Present Invention The amorphous curcumin-containing powdery composition produced in Example 1 was used to obtain the Raman spectrum of the powdery composition of the present invention in accordance with Raman spectroscopy (780 nm, nominal laser output level 10 mW) and the X-ray diffraction pattern of the powdery composition of the present invention recorded in the reflection/transmission mode. The results are shown in FIG. 1 and FIG. 2.

FIG. 2 shows that curcumin in the composition of the present invention is maintained in an amorphous state. Curcumin in the composition of the present invention is also shown to have a unique Raman spectrum as shown in FIG. 1.

Figure 3:
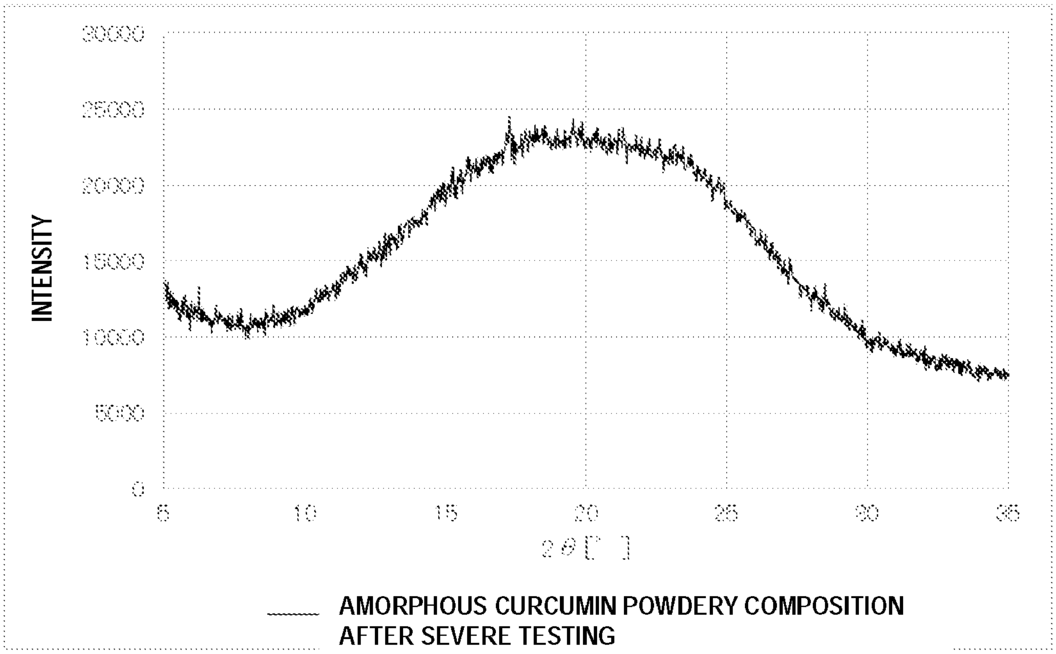
FIG. 3 illustrates storage stability of the amorphous curcumin compound-containing powdery composition of the present invention.

[Test Example 2] Storage Stability of Powdery Composition of Present Invention The powdery composition produced in Example 1 was stored at 37° C. and a relative humidity of 100° for 4 days. The results are shown in FIG. 3. FIG. 3 shows that the curcumin compound is maintained in an amorphous state and stable even under severe conditions at a relative humidity of 100%.

[Test Example 3] AUC and Cmax of Amorphous Curcumin-Containing Powdery Composition of Present Invention The amorphous curcumin-containing powdery composition produced in Example 1 was used. In Comparative Example 1, a commercial curcumin formulation which was said to have high absorbability was used. In Comparative Example 2, a product obtained by completely melting curcumin, then cooling melted curcumin at room temperature, and finely grinding the resulting amorphous curcumin with a tornado mill (without wet grinding together with a hydrophilic polymer) was used.

The plasma curcumin concentration was measured by the following method using heparin plasma obtained by collecting about 0.2 mL of blood from the jugular vein of test animals (rats) without anesthesia at 0.25 hours, 0.5 hours, 1 hour, 2 hours, 4 hours, and/or 6 hours after start of administration.

a. Pre-Treatment

To 20 μL of the collected plasma, 100 μL of 0.1 M acetate buffer (pH 5.0) and 10 μL of β-glucuronidase solution (about 68,000 units/mL) were added. The mixture was kept at 37° C. for 1 hour. Subsequently, 10 μL of 50% (v/v) methanol containing 20 ng/mL of Mepronil, an internal standard, and 0.5 mL of chloroform were added. The mixture was stirred with a vortex mixer for 1 minute and then mixed with an ultrasonic generator for 15 minutes to perform an extraction process. The extraction process liquid was separated into a chloroform layer and an aqueous layer by centrifugation (13,000×g, 5 min, room temperature). The separated aqueous layer was further subjected to an extraction process in which extraction was performed by adding chloroform in the same manner as described above. Next, the chloroform layer was collected and dried to solid by distilling the solvent off using a vacuum centrifugal concentrator, and 100 μL of 50% (v/v) methanol was added thereto, followed by centrifugation (13,000×g, 5 min, room temperature). The supernatant was then collected.

b. Measurement Method

The plasma curcumin concentration was measured by analyzing 2 μL of the prepared supernatant using LC-MS/MS (available from Bruker). The LC-MS/MS analysis conditions were as follows: the LC column was Sunshell C18 (2.1×100 mm, 2.6 μm, available from Chromanik Technologies), the column temperature was 40° C., the flow rate was 0.4 mL/min, the mobile phase was A: 0.1% formic acid aqueous solution, B: 0.1% formic acid/acetonitrile, and the gradient elution was performed under the conditions shown in Table 2. The MS analysis conditions were as follows: the ionization mode was Electron Spray thermo ionization (ESI), positive, the measurement mode was Multiple Reaction Monitoring (MRM), and the evaluation was performed with curcumin 369.1→177.2 (m/z) and Mepronil 270→119 (m/z).

The calibration curve used to quantitatively determine the curcumin content in the sample was obtained by performing measurement under the same conditions as described above using various standard solutions (curcumin concentration: 0.9 to 225 ng/mL) prepared by adding 10 μL of a 50% ethanol solution containing 20 ng/mL of Mepronil to 90 μL of a 50% (v/v) methanol solution (curcumin standard solution) containing 1.0, 2.0, 3.9, 7.8, 15.6, 31.3, 62.5, 125, or 250 ng/mL of curcumin.

TABLE 2

| | Time(min) | | | | | |
|---|---|---|---|---|---|---|
| | 0 | 0.75 | 2 | 2.5 | 2.6 | 5 |
| % B | 55 | 55 | 95 | 95 | 55 | 55 |

Table 3 shows the plasma curcumin concentration (ng/mL), the maximum blood concentration (Cmax (ng/mL)), and the area under the blood concentration-time curve (AUC (ng/mL, 0 to 6 hrs)). The oral absorbability of the amorphous curcumin obtained in the present invention is found to be much higher than that of Comparative Example 2 and the commercial curcumin formulation (Comparative Example 1).

The Cmax of the powdery composition of the present invention is found to be reached more quickly than those of other curcumin compounds and reached 30 minutes after administration. In addition, the Cmax of the powdery composition of the present invention was 9.6 times higher than the Cmax of the commercial curcumin formulation (Comparative Example 1).

TABLE 3

| | AUC (ng/mL · 0-6 hr) | Cmax (ng/mL) |
|---|---|---|
| Comparative Example 1 | 296 (1.0) | 101 (1.0) |
| Comparative Example 2 | 292 (0.99) | 85 (0.84) |
| Example 1 | 1089 (3.7) | 970 (9.6) |

The invention claimed is:

1. A powdery composition comprising an amorphous curcumin compound and a hydrophilic modified starch, wherein the powdery composition has a Raman spectrum including peaks at wavenumbers of 1630, 1599, 1428, and 1243 (express in ±2 $cm^{-1}$) in accordance with FIG. 1 and an X-ray powder diffraction (XRPD) pattern in accordance with FIG. 2, wherein a weight ratio of the amorphous curcumin compound to the hydrophilic modified starch is 1:2 to 2:1.

2. The powdery composition according to claim 1, wherein the curcumin compound is at least one selected from curcumin, bisdemethoxycurcumin, demethoxycurcumin, and tetrahydrocurcumin.

3. The powdery composition according to claim 1, wherein a weight ratio of the amorphous curcumin compound to the hydrophilic modified starch is 1:1.8 to 1.8:1.

4. A method for producing the powdery composition according to claim 1, the method comprising wet-grinding a mixture of an amorphous curcumin compound and a hydrophilic modified starch, and then forming a fine powder from the wet-ground mixture.

5. The production method according to claim 4, wherein the amorphous curcumin compound is obtained by heat-melting a curcumin compound and then roughly grinding the curcumin compound.

6. The production method according to claim 4, wherein a process for forming the fine powder involves freeze drying.

7. The production method according to claim 4, wherein a mixing weight ratio of the amorphous curcumin compound to the hydrophilic modified starch is 1:1.8 to 1.8:1.

* * * * *